(12) United States Patent
Ludvig et al.

(10) Patent No.: US 10,953,391 B2
(45) Date of Patent: Mar. 23, 2021

(54) MODIFIED Y-ZEOLITE/ZSM-5 CATALYST FOR INCREASED PROPYLENE PRODUCTION

(71) Applicant: Albemarle Europe SPRL, Louvain-la-Neuve (BE)

(72) Inventors: Maria Margaret Ludvig, Seabrook, TX (US); Erja Paivi Helena Rautiainen, Leusden (NL); Albert Carel Pouwels, Amersfoort (NL)

(73) Assignee: ALBEMARLE EUROPE SPRL, Louvain-la-Neuve (BE)

( * ) Notice: Subject to any disclaimer, the term of this patent is extended or adjusted under 35 U.S.C. 154(b) by 0 days.

(21) Appl. No.: 16/201,237

(22) Filed: Nov. 27, 2018

(65) Prior Publication Data

US 2019/0091669 A1 Mar. 28, 2019

Related U.S. Application Data

(63) Continuation-in-part of application No. 14/647,989, filed as application No. PCT/EP2013/077509 on Dec. 19, 2013, now Pat. No. 10,173,206.

(60) Provisional application No. 61/740,948, filed on Dec. 21, 2012.

(51) Int. Cl.

| | |
|---|---|
| *B01J 29/06* | (2006.01) |
| *B01J 29/80* | (2006.01) |
| *B01J 29/08* | (2006.01) |
| *B01J 29/40* | (2006.01) |
| *B01J 35/02* | (2006.01) |
| *C10G 11/05* | (2006.01) |
| *C10G 11/18* | (2006.01) |
| *C10G 11/16* | (2006.01) |
| *C10G 11/14* | (2006.01) |
| *C07C 4/06* | (2006.01) |
| *B01J 38/06* | (2006.01) |
| *B01J 38/12* | (2006.01) |
| *B01J 35/00* | (2006.01) |
| *B01J 29/90* | (2006.01) |

(52) U.S. Cl.
CPC ............. *B01J 29/80* (2013.01); *B01J 29/061* (2013.01); *B01J 29/084* (2013.01); *B01J 29/40* (2013.01); *B01J 35/023* (2013.01); *C07C 4/06* (2013.01); *C10G 11/05* (2013.01); *C10G 11/14* (2013.01); *C10G 11/16* (2013.01); *C10G 11/18* (2013.01); *C10G 11/182* (2013.01); *B01J 29/90* (2013.01); *B01J 35/0006* (2013.01); *B01J 38/06* (2013.01); *B01J 38/12* (2013.01); *B01J 2029/062* (2013.01); *B01J 2229/186* (2013.01); *B01J 2229/42* (2013.01); *C07C 2529/08* (2013.01); *C07C 2529/40* (2013.01); *C07C 2529/80* (2013.01); *C10G 2400/20* (2013.01)

(58) Field of Classification Search
CPC . B01J 29/084; B01J 29/40; B01J 29/80; B01J 29/061; B01J 2029/062; B01J 2229/42; B01J 35/0006; B01J 2229/186; B01J 35/023; B01J 38/12; C10G 2400/20; C10G 11/05; C10G 11/14; C10G 11/16; C10G 11/18; C10G 11/182; C07C 2529/40; C07C 2529/80; C07C 2529/08; C07C 4/06
USPC ............ 502/64, 67, 69, 71, 77, 79; 208/113, 208/118, 119, 120.25; 585/613, 649, 648, 585/653
See application file for complete search history.

(56) References Cited

U.S. PATENT DOCUMENTS

| | | | |
|---|---|---|---|
| 3,758,403 A | 9/1973 | Rosinski et al. | |
| 4,191,638 A | 3/1980 | Plank et al. | |
| 4,289,606 A | 9/1981 | Gladrow et al. | |
| 4,309,280 A * | 1/1982 | Rosinski ............... | B01J 29/40 208/120.01 |
| 4,340,465 A | 7/1982 | Miller et al. | |
| 4,927,523 A * | 5/1990 | Donnelly ............... | C10G 11/18 208/120.01 |
| 4,994,424 A * | 2/1991 | Leib ...................... | B01J 8/0015 208/113 |
| 5,254,785 A | 10/1993 | Rosenfeld et al. | |
| 5,366,948 A | 11/1994 | Absil et al. | |
| 5,997,728 A * | 12/1999 | Adewuyi ............... | C10G 11/05 208/113 |

(Continued)

FOREIGN PATENT DOCUMENTS

| | | |
|---|---|---|
| CN | 1566274 A | 1/2005 |
| EP | 1795259 A1 | 6/2007 |

(Continued)

OTHER PUBLICATIONS

Degnan et al., "History of ZSM-5 fluid catalytic cracking additive development at Mobil", Microporous and Mesoporous Materials 35-36 (2000), pp. 245-252.*

(Continued)

*Primary Examiner* — Elizabeth D Wood

(74) *Attorney, Agent, or Firm* — Nathan C. Dunn; Marcy M. Hoefling; Troy S. Kleckley

(57) ABSTRACT

Provided is a Fluid Catalytic Cracking catalyst composition having increased propylene production with respect to other Fluid Catalytic Cracking catalysts (measured at constant conversion). The catalyst composition comprises a particulate which comprises (a) non-rare earth metal exchanged Y-zeolite in an amount in the range of about 5 to about 50 wt %, based upon the weight of the particulate; and (b) ZSM-5 zeolite in an amount in the range of about 2 to about 50 wt %, based upon the weight of the particulate.

15 Claims, 4 Drawing Sheets

(56) References Cited

U.S. PATENT DOCUMENTS

| | | |
|---|---|---|
| 6,210,562 B1 | 4/2001 | Xie et al. |
| 6,436,364 B1 | 8/2002 | Chiyoda et al. |
| 6,566,293 B1 | 5/2003 | Vogt et al. |
| 6,858,556 B2 | 2/2005 | Kuvettu et al. |
| 2004/0045285 A1 | 3/2004 | Penetrante et al. |
| 2005/0205464 A1* | 9/2005 | Hu .................. C10G 11/18 208/113 |
| 2007/0060780 A1 | 3/2007 | Stamires et al. |
| 2008/0093263 A1* | 4/2008 | Cheng .................. B01J 29/80 208/114 |
| 2009/0325786 A1 | 12/2009 | Liu et al. |
| 2010/0145127 A1 | 6/2010 | Xie et al. |
| 2010/0288675 A1 | 11/2010 | Long et al. |
| 2011/0163002 A1* | 7/2011 | White .................. B01D 61/362 208/95 |
| 2014/0080697 A1* | 3/2014 | Long .................. B01J 29/005 502/65 |

FOREIGN PATENT DOCUMENTS

| | | |
|---|---|---|
| EP | 2184335 A1 | 5/2010 |
| WO | 2006/050487 * | 5/2006 |
| WO | 2006/067104 A1 | 6/2006 |
| WO | 2007/005075 A1 | 1/2007 |
| WO | 20011/149763 * | 12/2011 |
| WO | 2013/005225 A1 | 1/2013 |

OTHER PUBLICATIONS

ACS Symposium Series, "Increasing Motor Octanes by Using ZSM-5 in Catalytic Cracking", M. Joan Comstock, Series Editor, Chapter 4, 1991, pp. 45-55.

W. Jia et al., "Synthesis of Y/ZSM-5 Composite Molecular Sieve with Ethylenediamine as a Template Agent", Petrochemical Technology, 2006, vol. 35, No. 9, pp. 832-836.

Niwa, Miki, et al., "Acidity and Cracking Activity on MgHY Zeolite", Microporous and Mesoporous Materials, 146, 2011, pp. 208-215.

B. Shen et al., "Studies on Application of ZSM-5/Y Composite Molecular Sieve in Hydrocarbon Catalytic Cracking Catalysts" J. Fuel Chemistry and Technology, 2004, vol. 32, No. 6, pp. 745-749.

S. Xu et al., "Preparation of ZSM-5/Y composite structure molecular sieve and exploration of the formation mechanism of the composite structure thereof", New Chemical Materials, 2012, vol. 40, No. 10, pp. 96-105.

Y. Xu et al. Catalyst Design and Catalytic Process. Beijing: Chemical Industry Press, 2003, pp. 191-193.

* cited by examiner

MODIFIED Y-ZEOLITE/ZSM-5 CATALYST FOR INCREASED PROPYLENE PRODUCTION

REFERENCE TO RELATED APPLICATIONS

This application is a Continuation of U.S. application Ser. No. 14/647,989, filed May 28, 2015, now U.S. Pat. No. 10,173,206, which is the National Stage of International Patent Appln. No. PCT/EP2013/077509, filed on Dec. 19, 2013, which in turn claims the benefit of U.S. Provisional Patent Appln. No. 61/740,948, filed on Dec. 21, 2012, the disclosures of which are incorporated herein by reference.

FIELD OF THE INVENTION

The present invention pertains to a catalyst composition and its use in a process for the cracking or conversion of a feed comprised of hydrocarbons, such as, for example, that obtained from the processing of crude petroleum, to a mixture high in propylene.

BACKGROUND

Fluidic Catalytic Cracking units are playing an increasingly important role in the production of propylene. The use of Y-zeolites in conjunction with pentasil zeolites, in particular, ZSM-5, has led to increases in the amount of propylene which can be produced from petroleum fraction feedstocks such as deep cut gas oil, vacuum gas oil, thermal oil, residual oil, cycle stock, whole top crude, tar sand oil, shale oil, synthetic fuel, heavy hydrocarbon fractions, such as those derived from the destructive hydrogenation of coal, tar, pitches, asphalts, hydrotreated feedstocks derived from any of the foregoing, and the like. Such Y-zeolites are generally doped or exchanged with rare-earth metals such as Lanthanum, Cerium, Neodymium and Praseodymium. These "rare-earth exchanged" zeolites are preferred because they have a high percentage of conversion which, it has been thought, is necessary in order to obtain high amounts of gasoline fraction which is generally thought to be necessary in order to maximize the amount of propylene which is produced by further cracking by the ZSM-catalyst.

However, such rare earth zeolites have reached a maximum in the amount of propylene that a given combination of rare earth-exchanged zeolites can generate in the co-presence of ZSM-type zeolites. It has heretofore been thought that other types of catalyst systems would have to be employed in order to get further gains in the amount of propylene with respect to the amounts produced by Y-zeolite/ZSM catalytic systems. While other types of dopants have been tried, many reduced the rate of conversion by the Y-zeolite, giving rise to overall efficiency considerations.

BRIEF DESCRIPTION OF THE INVENTION

However, it has been found that when Y-zeolites are exchanged with non-rare earth (NRE) metals, such as, for example, alkaline earth metals, and in particular, magnesium, the NRE-exchanged Y-zeolites can be used with ZSM-type zeolites to give increased amounts of propylene with respect to rare earth (RE) exchanged Y-zeolite catalyst systems at equivalent levels of conversion. This holds true despite the fact that the NRE-exchanged Y-zeolites have been shown to have a lower cracking efficiency (lower overall conversion) than RE-exchanged Y-zeolites.

Furthermore, the use of NRE-exchanged Y-zeolites in a single particle combination with auxiliary pentasil zeolites, such as ZSM-5, has been discovered to be particularly effective at boosting propylene conversion efficiency with respect to two particle rare-earth doped catalyst systems. This holds true regardless of whether the two particle system comprises RE or NRE-exchanged Y-zeolite.

Dual catalyst systems containing Y- and ZSM-5 zeolites for use in FCC processes are known in the art. When the base FCC catalyst that contains the Y zeolite is modified with rare earth, the activity of the catalyst system generally increases but the overall yield of lower olefins, such as propylene, will be decreased. Without desiring to be bound by theory, it is thought that the reduced yield is due to the fact that RE-Y has an increased hydrogen transfer ability with respect to the unexchanged Y-zeolite (USY), which reduces the fraction of the product which gives propylene upon contact with the ZSM-5 catalyst component. This is true for both the one particle and the two particle systems; where ZSM-5 is either in the same particle or in a separate particle from the base FCC catalyst.

It has been found that Y-zeolite substitution with NRE metals, particularly alkaline earth metals, and more particularly magnesium, gives a higher proportion of propylene than dual catalyst systems containing unexchanged Y-zeolite-containing systems. This effect is surprising because NRE substitution of the Y-zeolite component generally has the effect of lowering Y-zeolite catalyst activity with respect to unexchanged systems.

The effect is especially strong when the NRE-exchanged Y-zeolite and ZSM-5 component are used as a single particle system in which each particle of the particulate catalyst contains both catalytic components (NRE-exchanged Y-zeolite and ZSM-5 zeolites). The overall implication is that when the non-rare-earth (NRE) exchanged zeolites are used instead of rare-earth (RE) exchanged zeolites, and the NRE-exchanged zeolite and the ZSM-5 zeolite are used together in a single particle, the proportion of propylene is increased for a given level of conversion with respect to a RE-exchanged system.

For the two particle system, the propylene for the Mg—Y is comparable to the system containing unexchanged Y-zeolite (USY) with respect to the propylene yield at constant conversion, which is higher than for RE exchanged Y system. However, it has been found that a two particle, NRE exchanged systems give a reduction in the yield of coke at constant conversion with respect to two particle unexchanged (USY) systems. It is known that REY systems tend to produce more coke than USY systems and thus by inference MgY will have lower coke production than a REY system at constant conversion. The inventive two-particle NRE system is therefore an improvement over the art by providing comparable propylene yield with less coke than the USY or RE-Y zeolite systems.

DETAILED DESCRIPTION OF THE INVENTION

Figure 1:
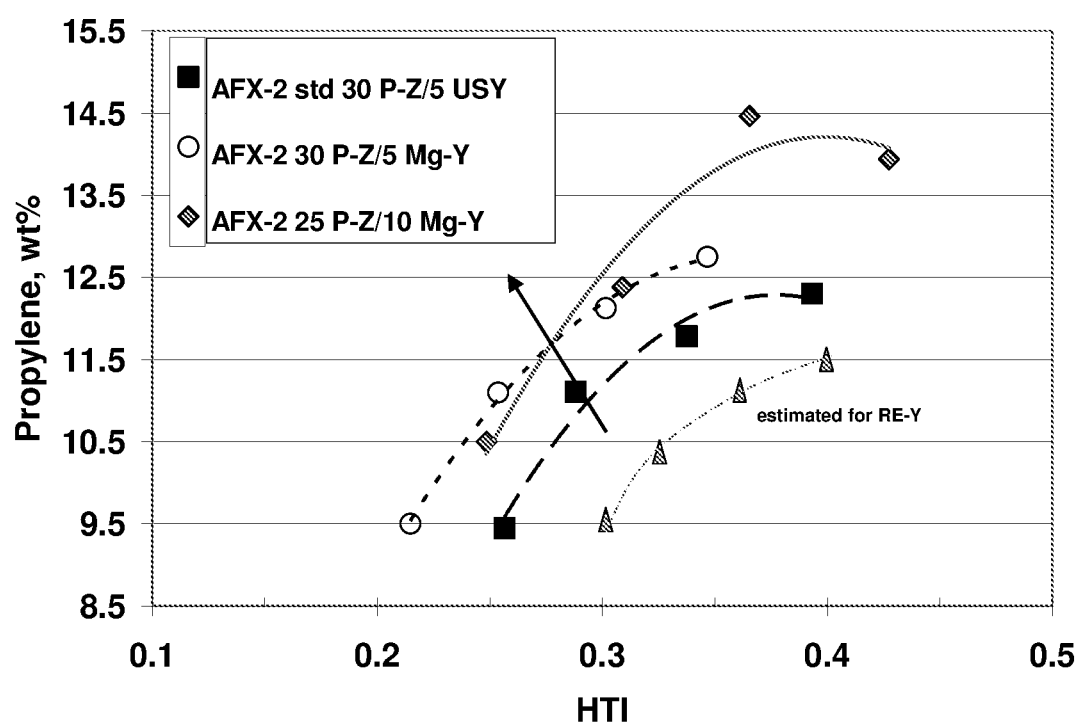
FIG. 1: A plot of propylene yield vs. hydrogen transfer index for a non-exchanged system and two different magnesium-exchanged systems, as well as an estimated plot for a Lanthanum (RE) exchanged system at a constant conversion of 72 wt %.

It is known that when a Y-zeolite FCC catalyst is modified with rare earth, the activity of the catalyst system will be increased, but the overall yield of propylene will be reduced. Applicant has found this to be true for both the one particle and the two particle systems; where ZSM-5 is either in the same particle or in a separate particle from the base Y-zeolite FCC catalyst.

We have found that Y-zeolite substitution with an NRE metal, such as an alkaline earth metal, more preferably magnesium, calcium or strontium, and most preferably magnesium, in a single particle system will yield more propylene than a USY-containing single particle system (see Example 1, which shows a higher propylene content at 73% conversion). Because the non-exchanged system yields more propylene at a constant conversion than a RE-exchanged system, it is also true that a NRE-exchanged system produces more propylene than a NRE-exchanged system, at equal conversion.

In the case of a two particle system having separate particles of the two component zeolites, the propylene for the NRE exchanged system (for example, containing Mg-exchanged Y-zeolite) is comparable to the USY-containing system. This result means that the propylene yield is greater than a RE-Y system. Remarkably, while the propylene yield may be lower than in the case of a single particle system, a reduction in the yield of coke at constant conversion was obtained with respect to an equivalent USY two particle system. It is known in the art that REY systems tend to produce more coke than USY systems and thus by, inference, MgY will have lower coke than a REY system at constant conversion.

Thus, Applicant has discovered that the use of a catalyst comprising a Y-zeolite exchanged with certain non-rare earth metals instead of rare-earth metals, can, when used in combination with a pentasil catalyst, increase the proportion of low molecular weight olefins relative to the use of Y-zeolites exchanged with rare earth metals. In particular, it has been found that Y-zeolites exchanged with magnesium, when used as cracking catalysts in combination with pentasil type catalysts such as ZSM-5, can be used to produce surprisingly high proportions of propylene. The effect is particularly pronounced in the case of a single particle embodiment. Remarkably, with respect to a two particle embodiment, such NRE-exchanged systems produce less coke than RE-exchanged systems.

Thus, in one embodiment, provided is a particulate FCC catalyst comprising:
a) a non-rare earth-exchanged (NRE) Y-zeolite; and
b) a ZSM class zeolite.

A non-rare earth-exchanged (NRE) Y-zeolite means a zeolite exchanged by a non-rare earth metal (as opposed to a non-metal element). Examples of such non-rare earth metals that may be used are alkali earth metals. Preferably, the NRE metals are the alkali earth metals magnesium, calcium and strontium. More preferably, the NRE metal is magnesium. The exchange of the NRE metal may be done by any suitable method known in the art such as ion-exchange or pore volume impregnation.

In another embodiment, the invention comprises an FCC catalyst composition comprising a particulate, said particulate comprising (a) non-rare earth metal exchanged Y-zeolite in an amount in the range of about 5 to about 50 wt %, based upon the weight of the particulate; and (b) ZSM-5 zeolite in an amount in the range of about 2 to about 50 wt %, based upon the weight of the particulate.

In one embodiment, the Y-zeolite and the ZSM components are copresent in the same particle, and the Y-zeolite comprising non-rare earth metal substitutions in an amount in the range of about 5 to about 30 wt %, based upon the weight of the particulate; and ZSM-5 in an amount in the range of about 5 to about 30 wt %, based upon the weight of the particulate. In an alternative embodiment, the Y-zeolite and the ZSM components are present in different particles, and the Y-zeolite comprising non-rare earth metal substitutions in an amount in the range of about 15 to about 40 wt %, based upon the weight of the particulate; and ZSM-5 in an amount in the range of about 25 to about 50 wt %, based upon the weight of the particulate.

In yet other embodiments, one or both components can be present as both mixed composition particles and/or single composition particles. Thus, in further independent embodiments, the invention comprises:

An FCC catalyst composition comprising a particulate, said particulate comprising (a) non-rare earth metal exchanged Y-zeolite in an amount in the range of about 25 to about 45 wt %, based upon the weight of the particulate; and (b) ZSM-5 zeolite in an amount in the range of about 25 to about 50 wt %, based upon the weight of the particulate;
1) wherein the catalyst composition is a mixture of at least two particulates, at least one first particulate comprising said Y-zeolite, and at least one second particulate comprising said ZSM-5 zeolite; or
2) wherein said catalyst composition comprises particles in which said Y-zeolite and ZSM-5 are present in the same particle.

In a still further embodiment, provided is a process for producing propylene from petroleum fraction feedstocks including one or more of deep cut gas oil, vacuum gas oil, thermal oil, residual oil, cycle stock, whole top crude, tar sand oil, shale oil, synthetic fuel, heavy hydrocarbon fractions, including those derived from the destructive hydrogenation of coal, tar, pitches, asphalts, or hydrotreated feedstocks derived from any of the foregoing, said process comprising the steps of:
a) providing an FCC catalyst composition comprising a particulate, said particulate comprising (a) non-rare earth metal exchanged Y-zeolite in an amount in the range of about 5 to about 25 wt %, based upon the weight of the particulate; and (b) ZSM-5 zeolite in an amount in the range of about 5 to about 35 wt %, based upon the weight of the particulate;
b) contacting the FCC catalyst with said petroleum fraction feedstock at a temperature in the range of from 400 to 650° C., with a dwell time in the range of from 0.5 to 12 seconds.

In another embodiment, the invention comprises a process as above, wherein the FCC catalyst composition improves the yield of propylene with respect to a process conducted as above, except using unexchanged Y-zeolite instead of non-rare earth exchanged zeolite on a weight-for weight basis, wherein the processes are compared at a feedstock conversion in the range of about 40-90 weight percent conversion. The weight percent conversion is the weight percent of the feed which is converted into coke, gas and gasoline.

In other embodiments, the invention comprises:

A process as above, wherein the ZSM-5 and non-rare earth metal exchanged Y-zeolite are in separate particulates, and wherein the ZSM-5 wt % of the catalyst composition is in the range of about 2 to about 15 wt %, based upon the combined weight of the particles comprising ZSM-5 and the particles comprising non-rare earth metal exchanged Y-zeolite;

A process as above, wherein the ZSM-5 and non-rare earth metal exchanged Y-zeolite are in separate particulates, and wherein the amount of non-rare earth metal exchanged Y-zeolite in the catalyst composition is in the range of about 15 to about 40 wt %, based upon the combined weight of the particles comprising ZSM-5 and the particles comprising non-rare earth metal exchanged Y-zeolite;

A process as above, wherein the ZSM-5 and non-rare earth metal exchanged Y-zeolite are present in the same particle, wherein the ZSM-5 wt % of the catalyst composition is in the range of about 5 to about 35 wt %, based upon the weight of the particles in which ZSM-5 and non-rare earth metal exchanged Y-zeolite are present;

A process as above, wherein the ZSM-5 and non-rare earth metal exchanged Y-zeolite are present in the same particle, and wherein the non-rare earth metal exchanged Y-zeolite in the catalyst composition is in the range of about 5 to about 30 wt %, based upon the weight of the particles in which ZSM-5 and non-rare earth metal exchanged Y-zeolite are present.

The FCC catalyst comprises a zeolite and a matrix. The zeolite proportions for both the one and two particle systems are given herein. The matrix is not expected to contribute significantly to the benefits of the inventive process. However, for both the one and two particle systems, preferably the matrix comprises alumina (0-35 wt %, more preferably, 4.5-25 wt %), a silica sol (0-25 wt %, more preferably 5-20 wt %) with the balance being kaolin or other type of clay which is typically present in the range of 15-55 wt %, and more preferably, in the range of 20-45 wt %. with the balance being largely or essentially kaolin clay. In the case of the two particle system, the matrix component amounts above apply to the combined matrices of both particle types.

One catalytic component is preferably an ultrastabilized faujasite Y- or preferably a USY-type zeolite. The FCC catalyst comprises a non-rare earth metal, present in its pores. In general, it is preferred that the NRE metal be magnesium. The magnesium can be exchanged onto the zeolite either by an ion exchange method using a magnesium-containing salt or applied by pore volume impregnation with a magnesium salt. The amount of magnesium salt, measured as magnesium oxide (MgO) is preferably in the range of from 0.25 to 3.0 wt %, and more preferably in the range of 1.25 to 2.75 wt %. In other embodiments, the catalyst composition comprises at least one non-rare earth metal, where the total non-rare earth metal content is in the range of about 0.2 to about 3 wt % percent. While a small degree of RE substitution is permissible, it is preferred that the RE metal content be less than about 0.5 wt %. In a more preferred embodiment, the Y-zeolite is essentially RE metal-free. By "essentially RE metal-free", it is meant that the RE-metal content is less than about 0.15 wt % of the Y-zeolite.

The ZSM-5-type catalyst can be a commercially available ZSM-5-containing additive, such as ZOOM, available from Albemarle Corporation. ZOOM contains about 40 wt % zeolite in a alumina-silica-phosphate matrix.

With respect to the single particle embodiment, it is preferred that the catalytic particles have an average diameter in the range of about 30 microns to about 200 microns. More preferred is an average diameter in the range of about 60 microns to about 100 microns. Preferred proportions of NRE-exchanged Y-zeolite mass to particle mass include ratios in the range of from about 5 to about 50 wt % Y-zeolite based upon the weight of the particulate. More preferred proportions of NRE-exchanged Y-zeolite mass to particle mass include ratios in the range of from about 5 to about 15 wt % Y-zeolite based upon the weight of the particulate. Preferred proportions of ZSM-class zeolite mass to particle mass include ratios in the range of from 2 to 50 wt % ZSM zeolite based upon the weight of the particulate. More preferred proportions of ZSM-class zeolite mass to particle mass include ratios in the range of from 10 to 35 wt % ZSM zeolite based upon the weight of the particulate. In a more preferred embodiment, the NRE-exchanged Y-zeolite and the ZSM zeolite have a weight ratio in the range of 0.16 to 1.0 weight Y-zeolite to ZSM zeolite. In an even more preferred embodiment, the NRE-exchanged Y-zeolite and the ZSM zeolite have a weight ratio in the range of 0.16 to 0.4 weight Y-zeolite to ZSM zeolite.

In the single particle embodiment, it is preferred that the Y-zeolite and ZSM-5 particulate which is used to make the single particle have an average particulate diameter in the range of about 1.9 to about 3.0 microns, and about 1.3 to about 2.3 microns, respectively.

With respect to the separate-particle embodiment, the particle size and proportion parameters are as follows. The NRE-exchanged Y-zeolite and the ZSM zeolite are used in a weight ratio in the range of 1.2 to 20 weight Y-zeolite to ZSM zeolite. In a preferred embodiment, the NRE-exchanged Y-zeolite and the ZSM zeolite have a weight ratio in the range of 1.8 to 5 weight Y-zeolite to ZSM zeolite.

Compounding zeolitic catalysts into particles is known in the art. A method outline of a convenient compounding follows. A USY-type zeolite is prepared. A NRE metal such as magnesium is then ion exchanged on to the zeolite to give a NRE Y-zeolite. The magnesium level on the zeolite, reported as MgO, can conveniently be in the range of 1.0 to 4 wt %, but the benefits of the invention may obtain outside the range. The Example below was performed with 1.6 wt % MgO. The NRE zeolite is then incorporated into a catalyst type particle with ZSM-5 zeolite. When ZSM-5 is in the same particle as the Mg-USY zeolite it is referred to herein as a one-particle system where if the ZSM-5 is present in the another particle, it is herein referred to as a two-particle system.

The physical properties of the one-particle system will be as with other FCC catalysts as known in the art, it should have proper attrition and ABD characteristics. The binding system of the catalyst can be silica or alumina type. The Table below is for a catalyst having an alumina binder; not all the chemical values are given where the amount of $TiO_2$ and $Fe_2O_3$ coming from the kaolin have been omitted along with the $SiO_2$ balance. All elements are reported as the oxides but are not necessarily found in that state in the catalytic composition.

TABLE

| | | |
|---|---|---|
| $AL_2O_3$, wt % | 50.81 | 51.94 |
| $Na_2O$, wt % | 0.356 | 0.39 |
| MgO, wt % | 0.21 | 0.27 |
| LOI (water content), wt % | 16.52 | 17 |
| SAMPLE PV (pore volume), cc | 0.376 | 0.394 |

TABLE-continued

| | | |
|---|---|---|
| APS (average particle size), microns | 70.84 | 72.9 |
| Attrition index | 2.25 | 2.15 |
| SAMPLE ABD (apparent bulk density), g/cc | 0.726 | 0.715 |
| SA BET (surface area), m$^2$/g | 234.7114 | 250.3199 |
| wt % P-ZSM-5 in particle | 30 | 25 |
| wt % Mg-Y in particle | 5 | 10 |

Referring to FIG. 1, it should be noted that for a given yield of propylene, the hydrogen transfer index is higher in the lanthanum exchanged system than it is in the non-exchanged system, which is higher than the measured NRE magnesium-exchanged systems. Example 1 gives the result of a study at 72 wt % conversion with three different single particle systems. One of the systems (denoted on the graph by square points), is an unexchanged system having both Y-zeolite (5 wt % based on the weight of the particulate) and ZSM-5 zeolite (30 wt % based on the weight of the particulate). Two of the systems (denoted by circles and diamonds, respectively) contain 30 wt % ZSM-5 and 5 wt % magnesium-exchanged Y-zeolite; and 25 wt % ZSM-5 and 10 wt % magnesium-exchanged Y-zeolite; respectively. The magnesium-exchanged Y-zeolite contained magnesium in 1.9 wt %, based upon the weight of the Y-zeolite. It should be noted that despite the shift in Mg—Y and ZSM-5 exchanged Y-zeolite concentration, the NRE-exchanged catalysts had very similar effects on hydrogen transfer index (refer to FIG. 1, which shows a strong shift toward higher propylene yield, despite the fact that one zeolite concentration was raised significantly, and the other zeolite concentration was lowered) and propylene yield (refer to Example: 14.33 and 14.41, versus 13.75 for unexchanged system). Thus, it is expected that in the case of NRE exchanged, ZSM-5 containing catalyst systems, the effect increased propylene production at a given wt % conversion would hold over a wide range of component zeolite concentrations.

Figure 2:
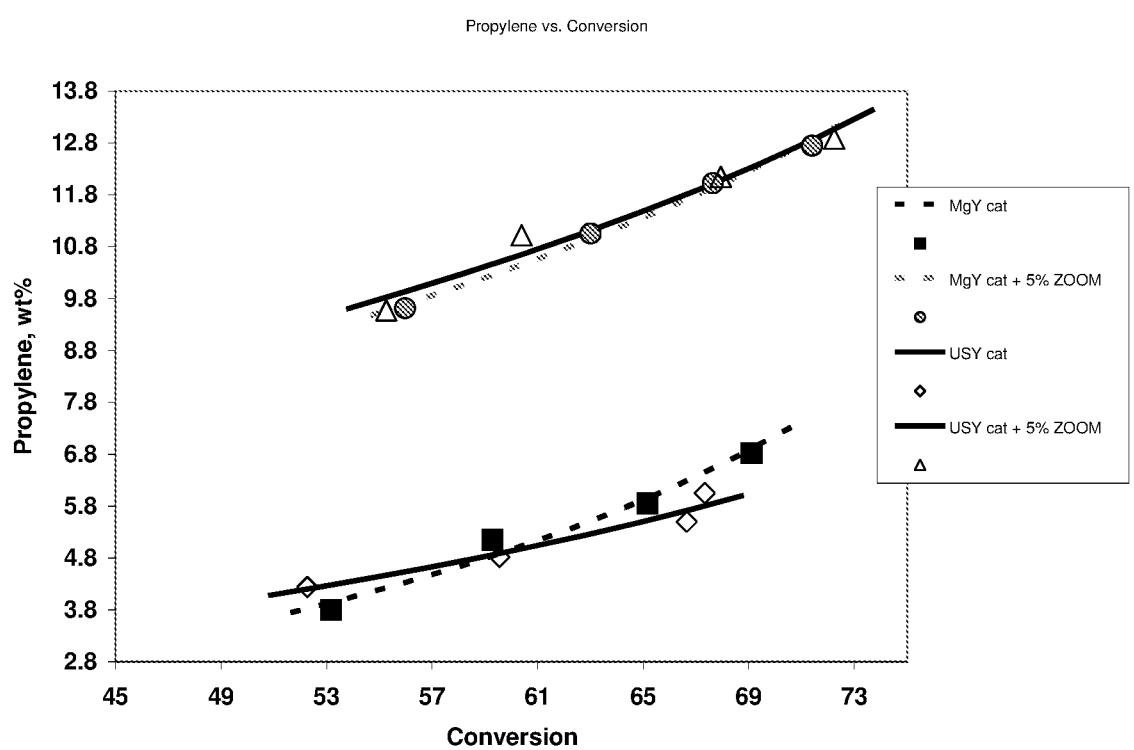
FIG. 2: A plot of propylene yield versus conversion for two particle systems, two of which are magnesium-exchanged systems (Mg—Y; Mg—Y and ZOOM, a ZSM-5 containing catalytic additive) and 2 systems analogous to the foregoing, but unexchanged.
Figure 3:
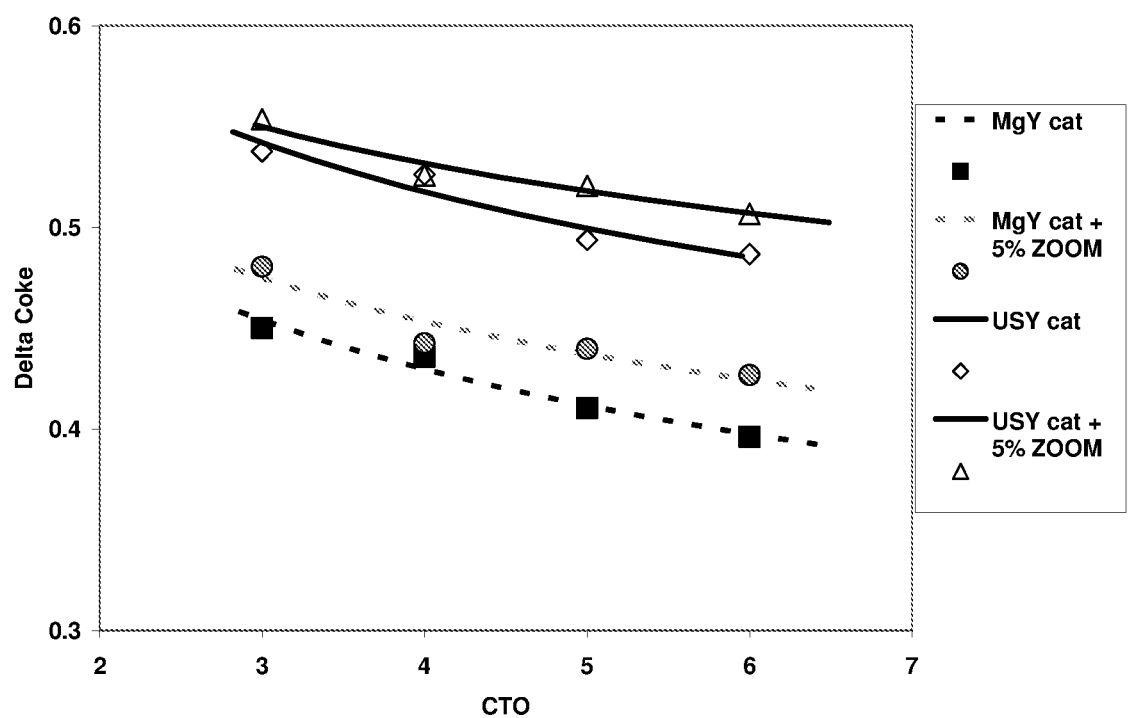
FIG. 3: A plot of coke production versus catalyst-to-oil ratio for the systems referenced in FIG. 2.
Figure 4:
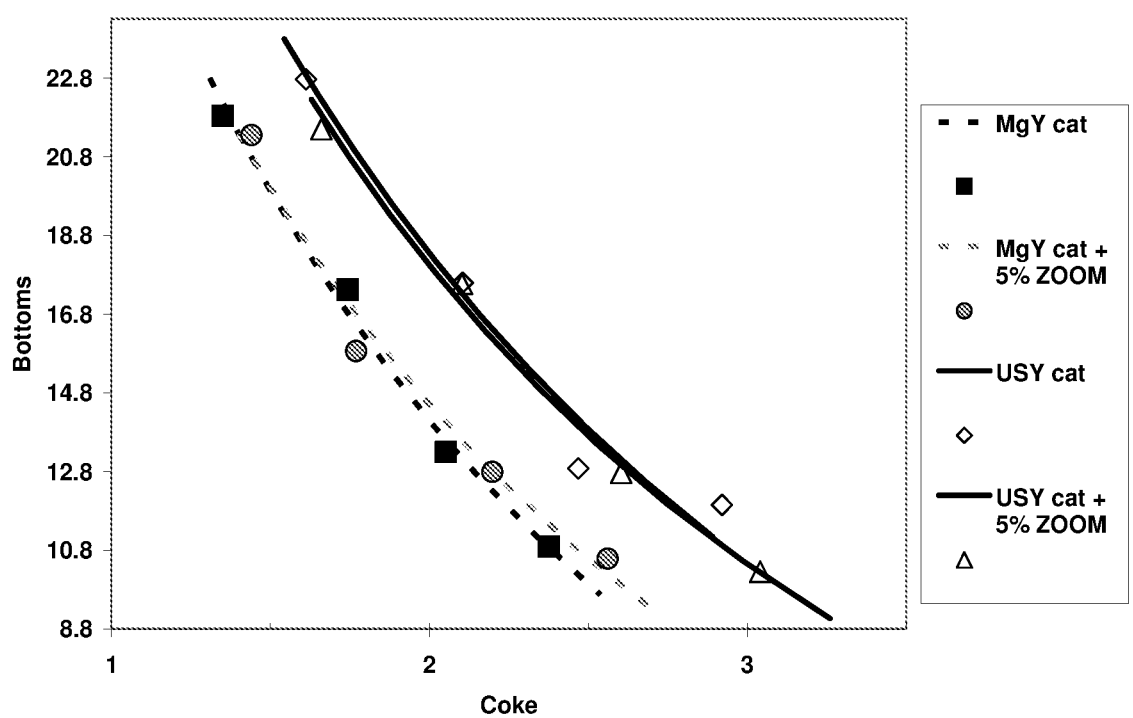
FIG. 4: A plot of bottoms versus delta coke for the systems referenced in FIG. 2.

Referring to FIG. 2, The Y-zeolites were used in with respect to two particle systems (i.e., systems in which the exchanged Y-catalyst and ZSM-5 catalyst are in separate particles) while the propylene yield may be lower than in the case of a single particle system, a reduction in the yield of coke at constant conversion was obtained with respect to an equivalent US-Y two particle system. As is known in the art, REY systems tend to produce more coke than USY systems and thus by, inference, MgY will have lower coke than a REY system at constant conversion. FIG. 2 shows a plot of propylene yield versus conversion for a two particle system, two of which are magnesium-exchanged systems (Mg—Y; Mg—Y and ZOOM, a ZSM-5 containing catalytic additive) and 2 systems analogous to the foregoing, but unexchanged. The Y-zeolite components were used in 25 wt % (exchanged) and 25 wt % (unexchanged). The ZSM-5 component was used in 5 wt % of ZSM-5 additive particle which contains 40% ZSM-5. Note that, unlike the one particle system, the difference in propylene yield at a given wt % conversion between the exchanged systems and the non-exchanged systems is not pronounced. However, the coke production of the catalyst systems was significantly reduced with respect to the unexchanged systems. Referring to FIG. 3, the delta coke, an index of coke production is significantly lower for the exchanged systems than for the unexchanged systems. The difference is pronounced over a wide range of catalyst-to-oil ratios, and remains relatively unchanged despite that fact that the overall trend is toward lower delta coke with higher catalyst-to-oil ratios. Referring to FIG. 4, coke production as a percentage of bottoms is lower with magnesium exchanged systems than with unexchanged systems. Again, the difference is pronounced over a wide range of catalyst-to-oil ratios, and remains relatively unchanged despite that fact that the overall trend is toward lower delta coke with higher catalyst-to-oil ratios.

The present invention provides a process for the production of increased amounts of low molecular weight olefins, and in particular, propylene, via a catalytic cracking process (i.e., the conversion of long-chain or large-size hydrocarbon compounds to shorter-chain or smaller hydrocarbon compounds). A range of catalytic apparatus can be used with the inventive catalyst. Included are fluidized bed, fixed bed, transfer line, and moving bed. While any of the foregoing can be used, the inventive catalyst is preferably used in a fluidized bed system with a Fluidized Catalytic Cracking process, although a Thermofor Catalytic Process can also be used. The catalyst can be used in processes in which the feedstock flow is concurrent or countercurrent to the flow of the catalyst. The inventive catalyst is particularly useful in systems which comprise a catalyst regeneration module or other means for partially or fully restoring the usefulness of the catalyst once its usefulness has been reduced by the accumulation of coke or other process products.

The process takes place at conditions known in the art to be suitable for catalytic cracking, i.e., at temperatures in the range of about 500 C to about 650 C, and pressures in the range of about atmospheric to about 5 atmospheres. In some cases, the pressure can be subatmospheric, as one of skill will recognize that petroleum fractions and mixtures which boil above temperatures at which thermal cracking could occur are preferably distilled under vacuum to promote vaporization.

The hydrocarbon feedstocks mixture to be subjected to cracking can include deep cut gas oil, vacuum gas oil, thermal oil, residual oil, cycle stock, whole top crude, tar sand oil, shale oil, synthetic fuel, heavy hydrocarbon fractions, such as those derived from the destructive hydrogenation of coal, tar, pitches, asphalts, hydrotreated feedstocks derived from any of the foregoing, and the like. One of skill will recognize that petroleum fractions and mixtures which boil above temperatures at which thermal cracking could occur are preferably distilled under vacuum to promote vaporization.

The process of the invention is particularly applicable to Fluid Catalytic Cracking (FCC). In the FCC process, the details of which are generally known, the catalyst, which is generally present as a fine particulate comprising over 90 wt % of the particles having diameters in the range of about 5 to about 300 microns, with a range of about 10 to about 200 microns more preferred (with the mean particle size about 65 to 95 microns), circulates between a cracking reactor and a regenerator. In the reactor portion, a hydrocarbon feedstock is gasified and directed upward through a reaction zone, such that the particulate catalyst is entrained and fluidized in the hydrocarbon feedstock stream. The hot catalyst, which is coming from the regenerator, reacts with the hydrocarbon feed which is vaporized and cracked by the catalyst. Typically temperatures in the reactor are 400-650° C. and the pressure can be under reduced, atmospheric or superatmospheric pressure, usually about atmospheric to about 5 atmospheres. The catalytic process can be either fixed bed, moving bed, or fluidized bed, and the hydrocarbon flow may be either concurrent or countercurrent to the catalyst flow. The process of the invention is also suitable for TCC (Thermofor catalytic cracking).

The cracking process produces coke deposits on the catalyst, which deactivates the catalyst. The cracked products are separated from the coked catalyst and the products are typically further separated into gaseous and liquid fractions. The coked catalyst is typically stripped of any volatiles with steam and then sent to the regenerator. The regenerator burns the coke off the catalyst with gas containing some oxygen to assist restoration of the catalyst activity and to heat the catalyst for the cracking reaction. The components removed from the catalyst by stripping and catalyst regeneration inactivate the catalyst, and thus their removal is essential to continued use of the catalyst. Typical temperatures in the regenerator are 600-850 C. The hot catalyst is then routed back to the reaction zone, where it is refluidized in the oncoming hydrocarbon stream, which can comprise, if desired, a portion of hydrocarbons which had previously contacted the catalyst, as well as hydrocarbons which are contacting the catalyst for the first time. The continuously incoming catalyst, which contains heat from the regeneration step, continuously supplies energy to the endothermic cracking reaction. In some units include the recirculation of the heavy gasoline or diesel fractions back to the unit to increase the LPG fraction.

Example

Prior to any lab testing the catalyst must be deactivated to simulate catalyst in a refinery unit, this is typically done with steam. These samples were deactivated with 100% steam at 788° C. for 20 hours. The deactivation step is known in the art, and is necessary to catalytic activity. In commercial FCC setting, deactivation occurs shortly after catalyst introduction, and does not need to carried out as a separate step. The propylene yield at a given conversion with respect to a Fluidized Bed Simulation is essentially the same as that which would be given in commercial practice. The Fluid microactivity test, or Fluidized-bed Simulation Test (FST) is a test known and generally accepted in the art for ascertaining the FCC cracking activity of a catalyst. The test is conducted with a series of four catalyst-to-feed ratios (CTO) which are obtained by varying the mass of catalyst present in the reactor, while using the same feed rate for all runs. The testing apparatus simulates the cracking of a known amount of a hydrocarbon feedstock of known amount and compositional characteristics. This small scale testing unit is a once through unit and operated approximately as in ASTM 5154-10. The feed for both Examples below is characterized as in Table 1. The reactor is in a hot furnace and the catalyst is added directly to the reactor followed by the feed injection, as outlined below.

TABLE 1

| Source Company | Crown |
|---|---|
| API | 25.8 |
| Spec. Gravity 60/60° F. | 0.8998 |
| Total Sulfur, wt % | 0.6439 |
| Total Nitrogen, ppmw | 1153 |
| Basic Nitrogen, ppmw | 342 |
| Conradson Carbon, wt % | 0.14 |
| Aniline Point ° F. | 188.3 |
| Refractive Index | 1.5000 |
| Na, ppmw | 1.0 |
| Ni, ppmw | 0.70 |
| V, ppmw | 0.06 |
| Fe, ppmw | 0.08 |
| Cu, ppmw | 0.05 |
| Distillation by D-1160 (or Simdis) | D-1160 |
| vol % | vol % |
| IBP | 442 |
| 5 | 557 |
| 10 | 608 |

TABLE 1-continued

| 20 | 667 |
|---|---|
| 30 | 705 |
| 40 | 740 |
| 50 | 778 |
| 60 | 819 |
| 70 | 855 |
| 80 | 889 |
| 90 | 953 |
| 95 | 1002 |
| EP | 1042 |
| Recovery % | 98.5 |
| Residue % | 1.5 |
| Viscosity @ 22 F. (CST) | |
| Viscosity @ 210 F. (CST) | 5.00 |
| Viscosity @ 506.4 F. (CST) | |
| Molecular Weight | 364 |
| API Procedure 2B4.1, % Cp | 55.6 |
| % Cn | 28.0 |
| % Ca | 16.4 |
| Molecular Weight | 386.8 |
| n-d-m Method, % Cp | 61.1 |
| % Cn | 22.2 |
| % Ca | 16.7 |
| % Total Cr | 38.9 |
| Watson K | 11.92 |

Example 1

One Particle System

Three single particle, two component catalyst formulations were tested. The catalyst to oil ratio was varied by using four different catalyst amounts (0.5, 6.0, 7.5 and 9.0 grams) of each catalyst. The Y-zeolite was exchanged with magnesium at about 1.9 wt % magnesium substitution based upon the weight of the Y-zeolite. The average particle size was about 75 microns.

In two samples, the magnesium-exchanged Y-zeolite content was about 5 and 10 wt %, respectively (based upon the weight of the particulate), and a ZSM-5 zeolite content of 30 and 25 wt %, respectively (based upon the weight of the particulate). In another sample, the sample catalyst formulation contained an unexchanged Y-zeolite (US-Y) having a wt % of about 5 (based upon the weight of the particulate), and a ZSM-5 zeolite content of 30 wt %, (based upon the weight of the particulate).

The particulate was loaded into the FST unit. The reaction temperature was fixed at 537° C. 1.5 grams of a hydrocarbon feed having the characteristics as listed in Table I are injected at a rate of 1.5 grams per minute. The gas and liquid products were collected and their component proportions were analyzed by GC. The weight percent conversion is the weight percent of the feed which is converted into coke, gas and gasoline. For each formulation, the catalyst-to-oil ratio was plotted against conversion, and the three formulations were compared at a conversion of 72 weight percent conversion. The results are given in Table 2.

Testing Results

One Particle System:

TABLE 2

| | AFX-2 std with USY | AFX-2 30 P-Z/ 5Mg-Y | AFX-2 25 P-Z/ 10Mg-Y |
|---|---|---|---|
| Conversion, wt % | 72.000 | 72.000 | 72.000 |
| Conv./(100 − Conv.) | 2.571 | 2.571 | 2.571 |
| Catalyst-to-Oil wt/wt | 7.627 | 7.603 | 5.712 |
| Delta Coke, wt % | 0.513 | 0.471 | 0.513 |

TABLE 2-continued

|  | AFX-2 std with USY | AFX-2 30 P-Z/ 5Mg-Y | AFX-2 25 P-Z/ 10Mg-Y |
|---|---|---|---|
| YIELDS, WT % | | | |
| Coke | 3.91 | 3.58 | 2.93 |
| Dry gas | 7.28 | 7.32 | 6.04 |
| Hydrogen | 0.30 | 0.29 | 0.20 |
| Hydrogen sulfide | 0.34 | 0.47 | 0.34 |
| Methane | 0.81 | 0.78 | 0.67 |
| Ethane | 0.74 | 0.69 | 0.58 |
| Ethylene | 5.1 | 5.1 | 4.3 |
| Propane | 6.03 | 5.32 | 4.21 |
| Propylene | 13.75 | 14.33 | 14.41 |
| n-Butane | 2.39 | 2.19 | 1.87 |
| Isobutane | 4.89 | 4.70 | 4.89 |
| C4 Olefins | 10.76 | 11.31 | 11.93 |
| LPG | 37.81 | 37.85 | 37.31 |
| Gasoline | 23.00 | 23.25 | 25.71 |
| LCO | 16.40 | 16.72 | 16.09 |
| Bottoms | 11.60 | 11.28 | 11.91 |
| Total | 100 | 100 | 100 |
| i-C4/C4= (HTI) | 0.4543 | 0.4156 | 0.4097 |

Example 2

Two Particle System

The catalyst-to-oil ratio was varied by performing four runs using four different catalyst amounts. About 4.5, 6.0, 7.5 and 9.0 grams of a two particle, two component catalyst were used in the four runs.

In two runs, the catalyst was composed of 95 wt % and 100 wt %, respectively (based upon the weight of the total particulate) of a particulate containing magnesium exchanged-Y-zeolite. The Y-zeolite was exchanged with magnesium at 1.9 wt % based on the weight of the Y-zeolite, and the Y-zeolite-containing particulate contained 25 wt % of the Mg-exchanged Y-zeolite. in one of the runs, the remainder of the two-particle blend (5 wt % based on the total weight of the total particulate) consisted of a ZSM-5 containing particulate (ZOOM) which was 40 wt % ZSM-5.

In the remaining two runs, the catalyst formulations were as in the first two runs, except that the Y-zeolite was unexchanged.

The Y-zeolite-containing particulate (exchanged or unexchanged) had an average particle size of about 75 microns, and the ZSM-5-containing particulate had an average particle size of about 85 microns. The overall average particle size was approximately about 75 microns. The reaction temperature was fixed at 537° C. 1.5 Grams of a hydrocarbon feed having the characteristics as listed in Table I are injected at a rate of 1.5 grams per minute. The gas and liquid products were collected and their component proportions were analyzed by GC. The weight percent conversion is the weight percent of the feed which is converted into coke, gas and gasoline:

100×[(weight of feed)−(weight of light cycle oil produced)−(weight of bottoms/residue formed, including coke on catalyst]/[weight of feed].

For each formulation, the catalyst-to-oil ratio was plotted against conversion, and the four formulations were compared at a conversion of 65 weight percent conversion. The results are given in Table 3.

The weight of the coke on the catalyst is measured by removing the catalyst from the reactor after the reaction and subjecting it to analysis by a LECO™ carbon analyzer.

The feed was a CROWN VGO feed and Table 1 shows the properties of this feed. The results are given in Table 2. Two Particle System:

TABLE 3

|  | MgY cat | MgY cat + 5% ZOOM | USY cat | USY cat + 5% ZOOM |
|---|---|---|---|---|
| Conversion, wt % | 65.000 | 65.000 | 65.000 | 65.000 |
| Catalyst-to-Oil wt/wt | 4.994 | 4.414 | 5.029 | 4.489 |
| Delta Coke, wt % | 0.412 | 0.446 | 0.499 | 0.525 |
| YIELDS, WT % | | | | |
| Coke | 2.06 | 1.97 | 2.51 | 2.35 |
| Dry gas | 2.24 | 3.63 | 2.44 | 3.93 |
| Hydrogen | 0.18 | 0.16 | 0.19 | 0.20 |
| Hydrogen sulfide | 0.34 | 0.34 | 0.34 | 0.34 |
| Methane | 0.67 | 0.66 | 0.73 | 0.72 |
| Ethane | 0.45 | 0.44 | 0.53 | 0.52 |
| Ethylene | 0.61 | 2.02 | 0.65 | 2.16 |
| Propane | 0.92 | 1.83 | 0.89 | 1.94 |
| Propylene | 5.91 | 11.35 | 5.50 | 11.48 |
| n-Butane | 0.63 | 0.98 | 0.67 | 0.99 |
| Isobutane | 3.11 | 3.32 | 2.57 | 3.01 |
| C4 Olefins | 7.75 | 11.03 | 7.64 | 11.00 |
| Gasoline | 42.38 | 30.89 | 42.79 | 30.30 |
| LCO | 21.44 | 20.21 | 21.21 | 20.17 |
| Bottoms | 13.56 | 14.79 | 13.79 | 14.83 |
| Total | 100 | 100 | 100 | 100 |

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation in its practice. Therefore the foregoing description is not intended to limit, and should not be construed as limiting, the invention to the particular exemplifications presented hereinabove. The claims below are incorporated into this specification by reference.

That which is claimed is:

1. An FCC catalyst composition comprising a mixture of at least two particulates,
    at least one first particulate comprising a Y-zeolite exchanged with a non-rare earth metal, wherein the Y-zeolite exchanged with a non-rare earth metal is in an amount in the range of about 15 to about 40 wt %, based upon the combined weight of the particulates, and
    at least one second particulate comprising a zeolite in a matrix, wherein the zeolite consists of a ZSM-5 zeolite, wherein the ZSM-5 zeolite is in an amount in the range of about 2 to about 15 wt %, based upon the combined weight of the first particulates comprising the Y-zeolite exchanged with a non-rare earth metal and the second particulates comprising a zeolite in a matrix, the zeolite consisting of ZSM-5, wherein the Y-zeolite exchanged with a non-rare earth metal and the ZSM zeolite are in a weight ratio in the range of about 1.2 to about 20 Y-zeolite to ZSM zeolite, and wherein the non-rare earth metal is magnesium, calcium or strontium.

2. An FCC catalyst composition as in claim 1 wherein said non-rare earth metal comprises magnesium.

3. An FCC catalyst composition as in claim 2 wherein said FCC catalyst composition is prepared by a process comprising magnesium/hydrogen ion exchange with an unexchanged Y-zeolite.

4. An FCC catalyst composition as in claim 2 wherein the magnesium is in an amount measured as magnesium oxide in the range of about 0.25 to about 3.0 wt % percent.

5. An FCC catalyst composition as in claim 1 wherein the FCC catalyst composition comprises a total non-rare earth metal content in the range of about 0.2 to about 3 wt % percent.

6. An FCC catalyst composition as in claim 1 wherein the Y zeolite is an ultrastabilized faujasite Y zeolite.

7. A process for producing propylene from a hydrocarbon feedstock, said process comprising the steps of:
a) providing an FCC catalyst composition comprising a mixture of at least two particulates,
at least one first particulate comprising a Y-zeolite exchanged with a non-rare earth metal, wherein the Y-zeolite exchanged with a non-rare earth metal is in an amount in the range of about 15 to about 40 wt %, based upon the combined weight of the particulates, wherein the non-rare earth metal is magnesium, calcium or strontium, and
at least one second particulate comprising a zeolite in a matrix, wherein the zeolite consists of a ZSM-5 zeolite, wherein the ZSM-5 zeolite is in an amount in the range of about 2 to about 15 wt %, based upon the combined weight of the first particulates comprising the Y-zeolite exchanged with a non-rare earth metal and the second particulates comprising a zeolite in a matrix, the zeolite consisting of ZSM-5,
wherein the Y-zeolite exchanged with a non-rare earth metal and the ZSM zeolite are in a weight ratio in the range of about 1.2 to about 20 Y-zeolite to ZSM zeolite; and
b) contacting the FCC particulate catalyst composition with the hydrocarbon feedstock, at one or more temperatures in the range of about 400 to about 650° C., with a dwell time in the range of about 0.5 to about 12 seconds.

8. A process as in claim 7 wherein contacting in b) takes place in a fluidized bed reactor.

9. A process as in claim 7 wherein the non-rare earth metal comprises magnesium.

10. A process as in claim 9 wherein the FCC catalyst composition comprises an amount of a magnesium salt measured as magnesium oxide in the range of from 0.25 to 3.0 wt %.

11. A process as in claim 7 wherein the resulting yield of propylene is greater, as compared with the resulting yield of propylene of the same process but modified to use an unexchanged Y-zeolite instead of said non-rare earth metal exchanged Y-zeolite on a weight-for-weight basis, the comparison being made at a feedstock conversion in the range of about 40 to about 90 weight percent conversion.

12. A process as in claim 7 wherein the FCC catalyst composition further comprises an amount of alumina in the range of 0 to about 35 wt %, an amount of silica sol in the range of 0 to about 25 wt %, and the remaining balance being clay.

13. A process as in claim 7 wherein:
the Y zeolite is an ultrastabilized faujasite Y zeolite; and/or
propylene is formed with a conversion efficiency in the range of about 4 to about 20 wt %, based upon the weight of the hydrocarbon feedstock.

14. A process as in claim 7 wherein the ZSM-5 is about 40 wt % of the second particulate.

15. An FCC catalyst composition as in claim 1 wherein the ZSM-5 is about 40 wt % of the second particulate.

* * * * *